(12) United States Patent
Zhang

(10) Patent No.: US 8,100,002 B2
(45) Date of Patent: Jan. 24, 2012

(54) ADHESION MEASURING APPARATUS

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 278 days.

(21) Appl. No.: 12/604,342

(22) Filed: Oct. 22, 2009

(65) Prior Publication Data
US 2010/0300193 A1   Dec. 2, 2010

(30) Foreign Application Priority Data
May 31, 2009  (CN) .......................... 2009 1 0302783

(51) Int. Cl.
*G01N 19/04* (2006.01)
*G01N 17/00* (2006.01)
*G01N 3/56* (2006.01)
*G01N 19/02* (2006.01)
*G01B 21/08* (2006.01)

(52) U.S. Cl. ..................... 73/150 A; 73/7; 73/150 R

(58) Field of Classification Search ................ 73/150 A, 73/7
See application file for complete search history.

(56) References Cited

U.S. PATENT DOCUMENTS

| 3,208,265 | A | * | 9/1965 | Rutledge ............................. 73/7 |
| 3,343,399 | A | * | 9/1967 | Baker ................................. 73/7 |
| 6,761,964 | B2 | * | 7/2004 | Tannenbaum ................ 428/213 |

* cited by examiner

*Primary Examiner* — Lisa Caputo
*Assistant Examiner* — Roger Hernandez-Prewitt
(74) *Attorney, Agent, or Firm* — Altis Law Group, Inc.

(57) ABSTRACT

A measuring apparatus is provided for measuring the coating adhesion of an edge or a corner of an object. The measuring apparatus includes a platform, a fixing assembly to fix the object, a supporting plate fastened to the platform, a loading mechanism pivotably attached to the supporting plate, a travelling limiting member fastened to the supporting plate to limit the pivoting angle of the loading mechanism, and a friction block installed to the loading mechanism and slidably abutting against and reciprocatingly rubbing the edge or corner of the object within a predetermined traveling distance. The predetermined traveling distance is limited by the traveling limiting member.

12 Claims, 6 Drawing Sheets

ADHESION MEASURING APPARATUS

BACKGROUND

1. Technical Field

The present disclosure relates to measuring apparatuses and, more particularly, to a measuring apparatus to measure a coating adhesive strength of an object.

2. Description of the Related Art

Surface characteristics are critical to consumer electronic products, especially for coated products, such as cell phones, moving picture experts group audio layer III (MP3) players, etc. Therefore, manufacturers of the consumer electronic products should measure good coating adhesive strength of their products, especially on the edges and the corners of the products, which are prone to be touched frequently.

In a conventional measuring method, a friction block with a predetermined weight is pressed onto an edge or a corner of a coated product to be measured, an operator manipulates the friction block to slide relative to the product back and forth repetitiously over a predetermined count, then to check whether the edges and corners are worn off. Thus, the coating adhesive strength of the product can be assessed.

One disadvantage of the conventional measuring method described above is that the operator cannot precisely control the angle and travelling distance of the friction block related to the to-be-measured product, therefore, accuracy and reliability of the measuring result is affected. Another disadvantage of the conventional method is that the measuring method is inefficient and laborious.

DETAILED DESCRIPTION

Figure 1:
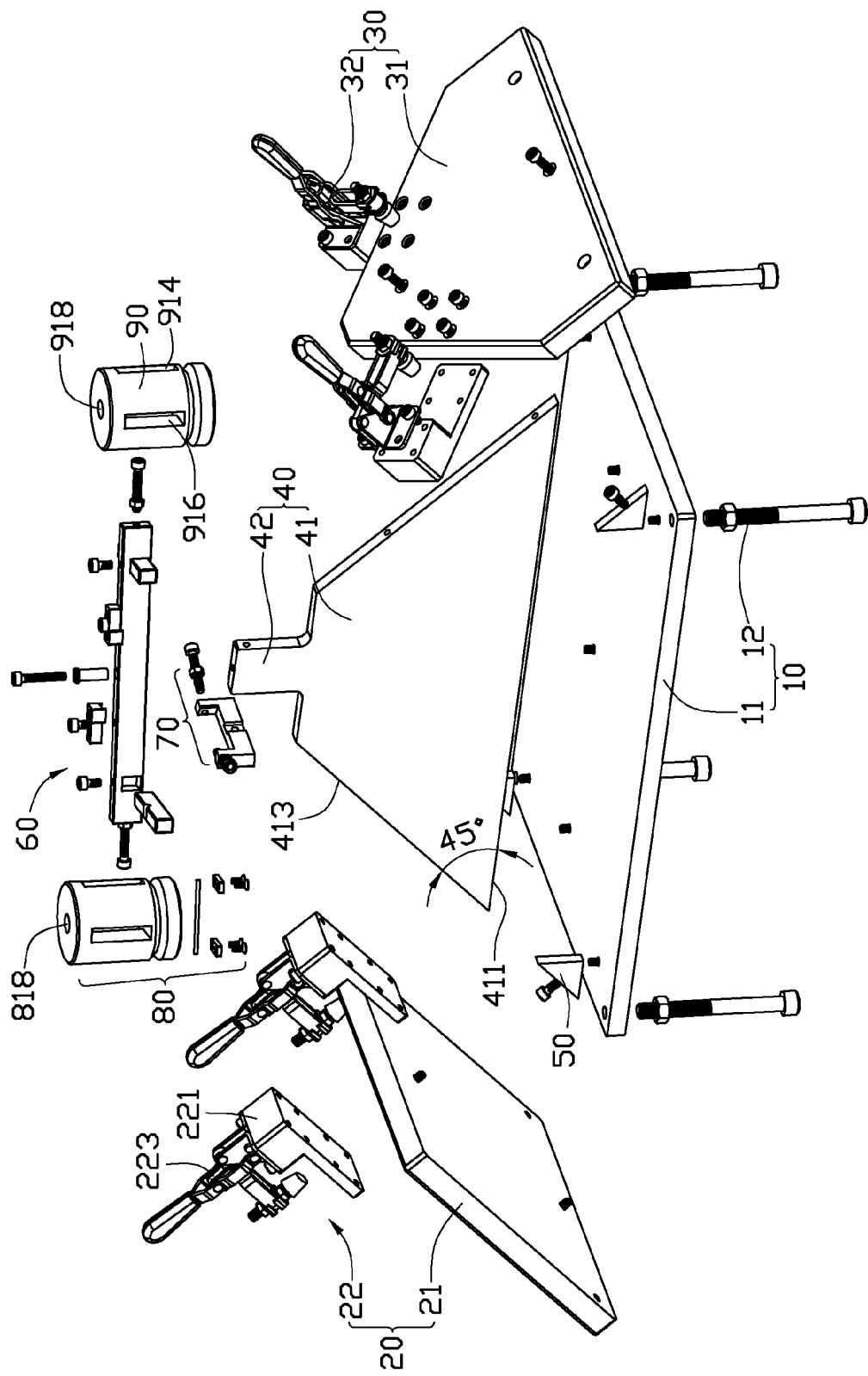
FIG. 1 is an exploded, isometric view of an exemplary embodiment of an adhesion measuring apparatus, the measuring apparatus includes a loading mechanism, a travelling limiting member, a first friction block, and a second friction block.
Figure 6:
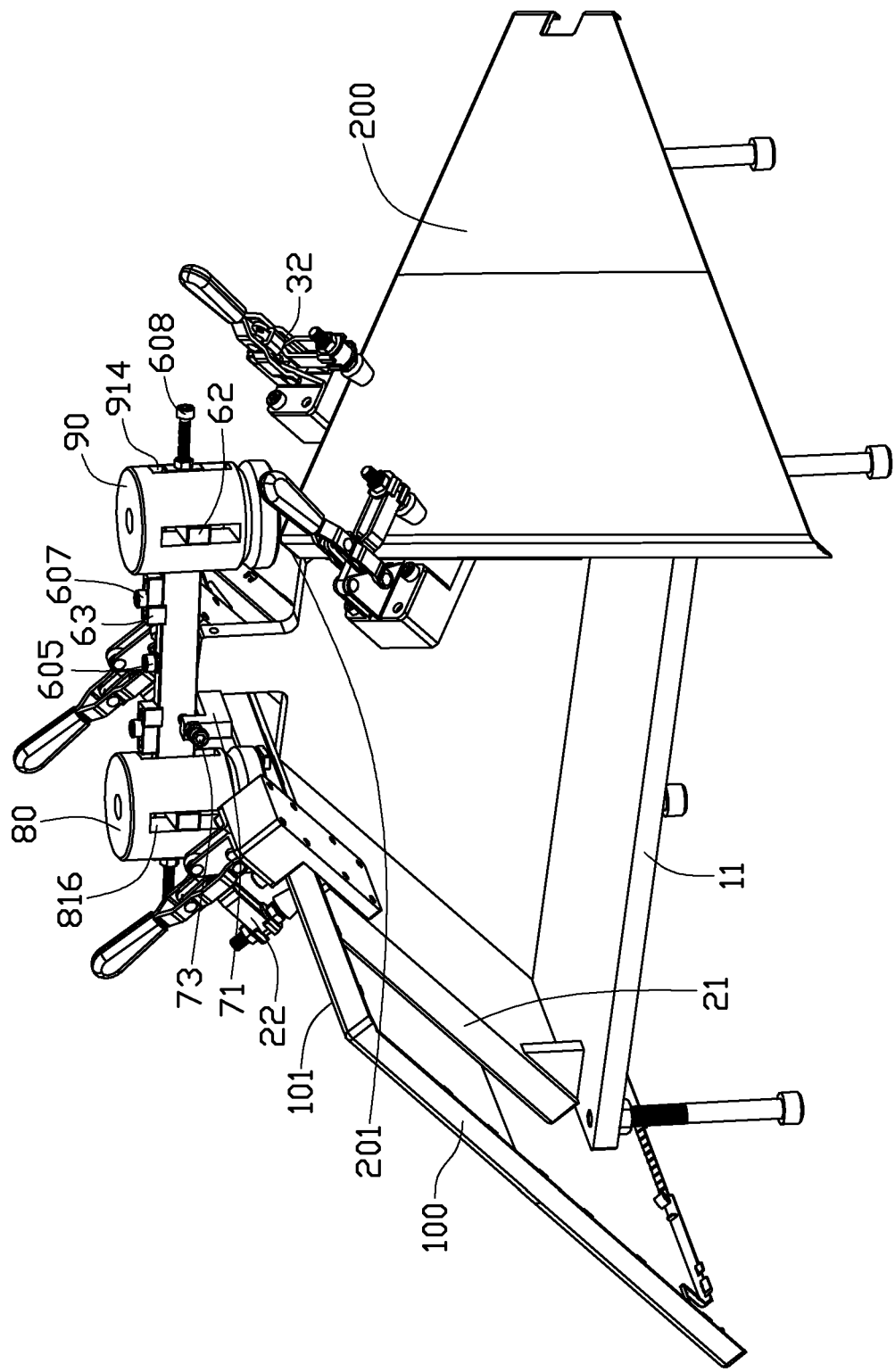
FIG. 6 is similar to FIG. 5, showing the measuring apparatus in a measuring state.

Referring to FIGS. 1 and 6, in an exemplary embodiment, an adhesion measuring apparatus is provided to measure coating adhesive strengths of an edge 101 of a first object 100 and a corner 201 of a second object 200. The measuring apparatus includes a platform 10, a first fixing assembly 20, a second fixing assembly 30, a supporting plate 40, two pairs of reinforcing members 50, a loading mechanism 60, a travelling limiting member 70, a first friction block 80, and a second friction block 90.

The platform 10 includes a rectangular placing board 11, and four supporting members 12 perpendicularly extending from four corners of the placing board 11. In one embodiment, each of the support members 12 includes a screw engaged in the placing board 11, and a nut engaging with the corresponding screw and abutting against a bottom of the placing board 11. The placing board 11 is horizontally positioned by adjusting the screws and nuts of the supporting members 12.

The first fixing assembly 20 includes a substantially square positioning plate 21, and two clamping members 22. Each of the clamping members 22 includes a mount 221, and a toggle clamp 223 attached to the mount 221. The toggle clamp 223 includes a clamping body, a handle and a linkage mechanism connected between the clamping body and the handle.

The second fixing assembly 30 includes a polygonal positioning plate 31, and two clamping members 32. The positioning plate 31 includes a rectangular portion and a trapezoidal portion extending from a side edge of the rectangular portion. Opposite lateral edges of the trapezoidal portion are orthogonal to each other. The clamping members 32 each are as same as the clamping members 22.

The support plate 40 includes a trapezoidal supporting portion 41, and a rectangular connecting portion 42 extending from a top edge of the supporting portion 41. In one embodiment, the angle between a bottom edge 411 and each of the opposite lateral edges 413 of the supporting portion is 45°. A plurality of screw holes is defined in the bottom edge 411 and opposite lateral edges 413 of the supporting portion 41, and a top edge and lateral edges of the connecting portion 42.

In one embodiment, each of the reinforcing members 50 is an isosceles right-angle triangle and includes a hypotenuse side and two right-angle sides.

Figure 2:
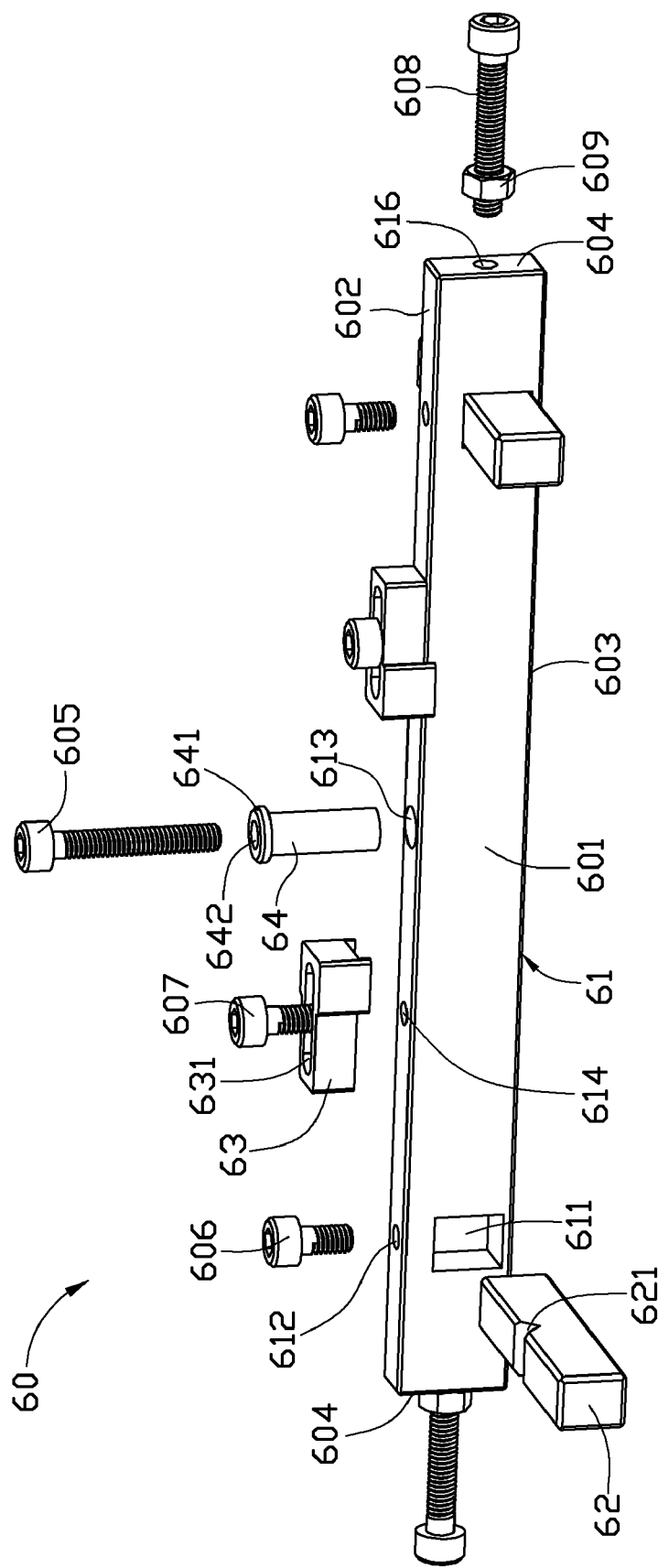
FIG. 2 is an exploded, enlarged view of the loading mechanism of FIG. 1.

Referring also to FIG. 2, the loading mechanism 60 includes a swing pole 61, two locking bars 62, two raising blocks 63, and a coupling member 64. The swing pole 61 has a rectangular cross section, and includes opposite sidewalls 601, a top wall 602, a bottom wall 603, and opposite end walls 604. Two coupling holes 611 are defined in the swing pole 61, through opposite sidewalls 601, and adjacent to opposite end walls 604 of the swing pole 61, respectively. Two screw holes 612 are defined in the swing pole 61, through the top wall 602 and the bottom wall 603, and adjacent to opposite end walls 604 of the swing pole 61, respectively. A pivoting hole 613 is defined in a middle of the swing pole 61, through the top wall 602 and the bottom wall 603. A fixing hole 614 is defined in the top wall 602 of the swing pole 61 and located between the pivoting hole 613 and each of the screw holes 612. Two screw holes 616 are respectively defined in the end walls 604 of the swing pole 61. Each of the locking bars 62 is a rectangular, with a locking groove 621 defined in a top thereof. Each of the raising blocks 63 has a T-shaped configuration. An oblong hole 631 is defined in the raising block 63, extending from a narrow portion thereof to a wide portion thereof. A pair of sliding flanges respectively extends from two opposite sides of the wide portion of the raising block 63. The coupling member 64 is substantially cylinder-shaped, and defines a though hole 642 extending along a central axis of the coupling member 64. The coupling member 64 forms a circumferential flange 641 at an end thereof.

Figure 3:
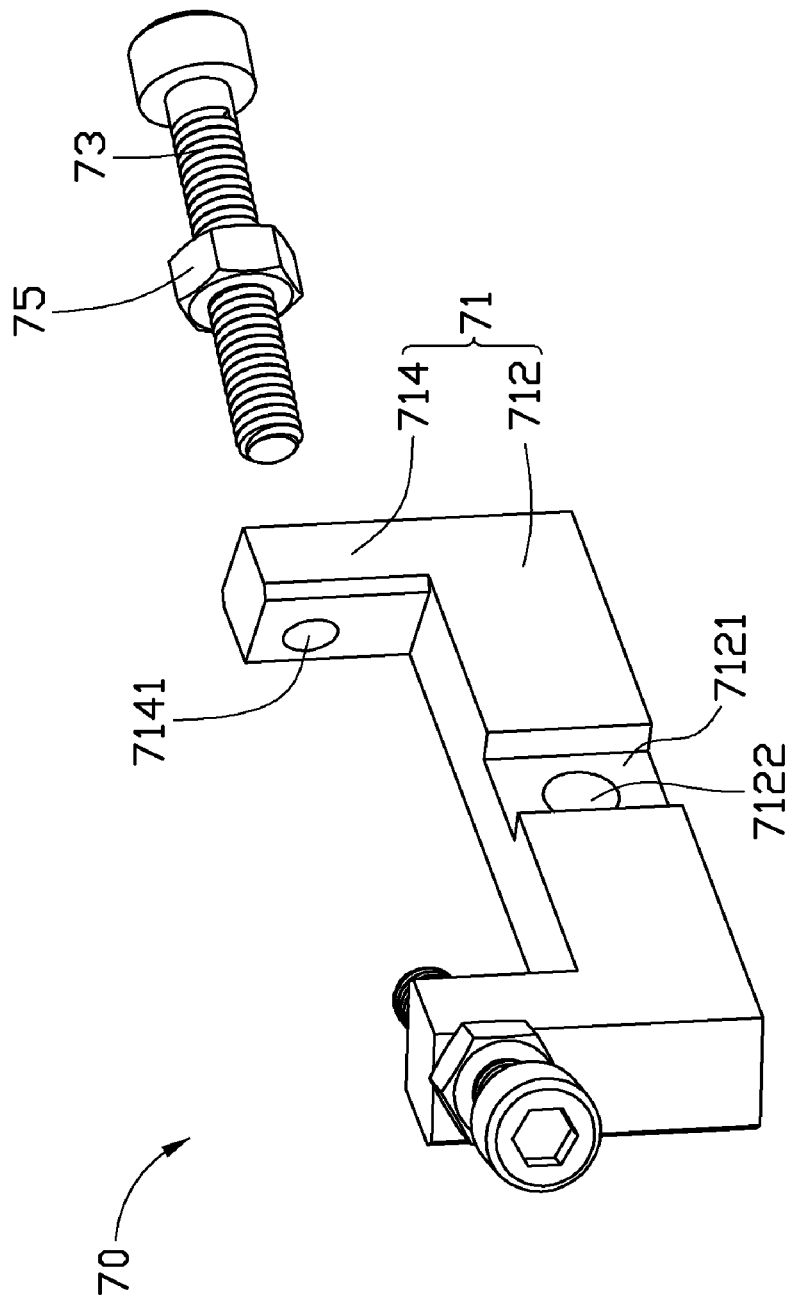
FIG. 3 is an exploded, enlarged view of the travelling limiting member of FIG. 1.

Referring to FIG. 3, the travelling limiting member 70 includes a positioning block 71, two screws 73, and two nuts 75 corresponding to the screws 73. The positioning block 71 is substantially U-shaped, and includes a mounting portion 712 and two blocking portions 714 perpendicularly extending from opposite ends of the mounting portion 712. An engaging groove 7121 is defined in a side surface of the mounting portion 712. A securing hole 7122 is defined in a bottom of the engaging groove 7121 of the mounting portion 712 and extends in a direction perpendicular to the side surface of the mounting portion 712. Two screw holes 7141 are respectively defined in the blocking portions 714.

Figure 4:
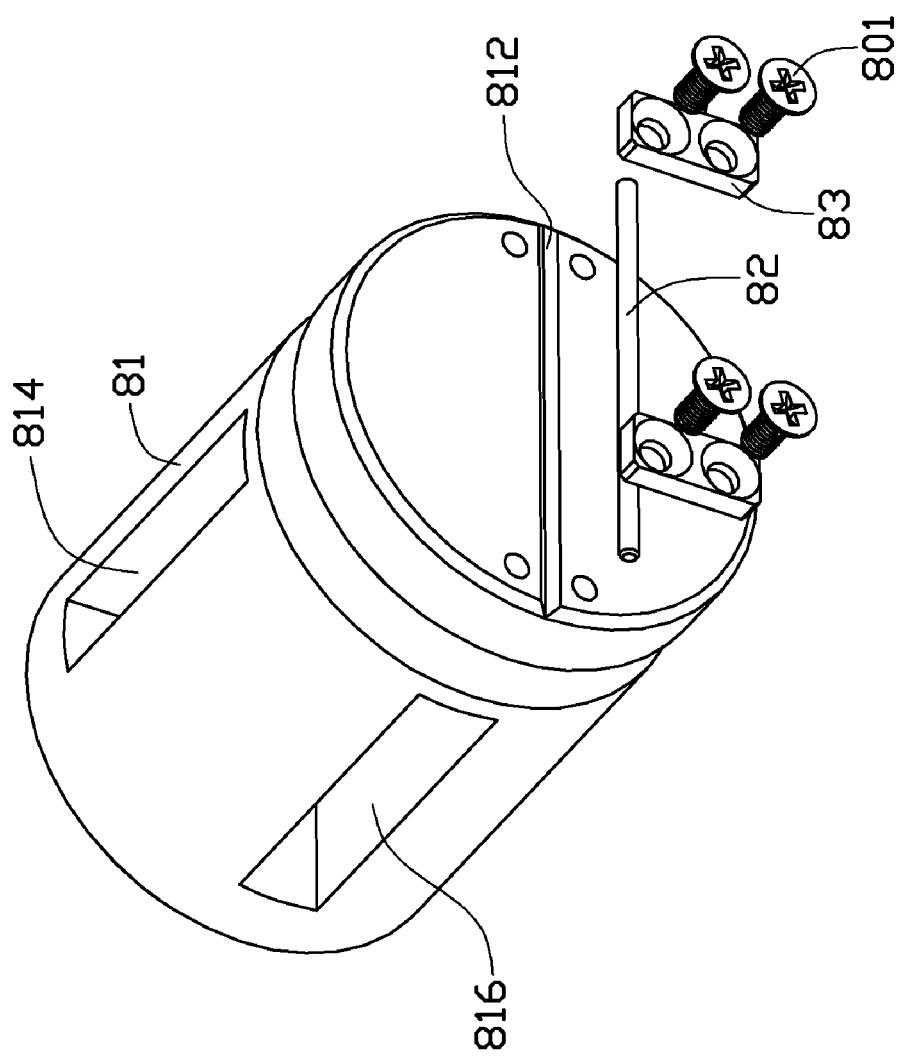
FIG. 4 is an exploded, enlarged view of the first friction block of FIG. 1, but shown from a different aspect.
Figure 5:
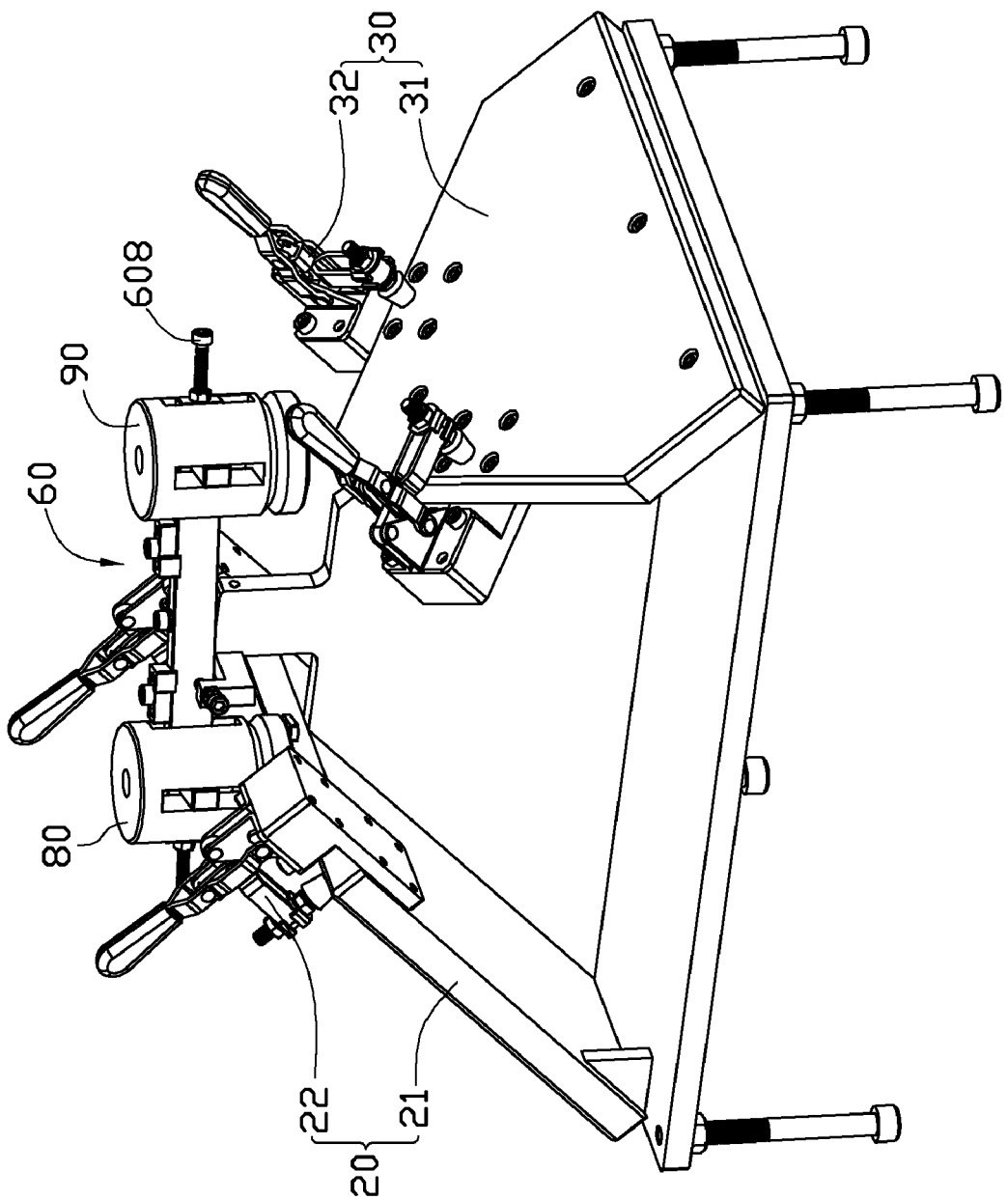
FIG. 5 is an assembled, isometric view of the measuring apparatus of FIG. 1.

Referring to FIGS. 1 and 4, the first friction block 80 includes a columnar body 81, a columnar friction bar 82, and two fixing members 83 for fixing the friction bar 82 to a bottom of the columnar body 81. A mounting groove 812 with a V-shaped cross section is defined in the bottom of the columnar body 81. Two pairs of fixing holes are defined in the bottom of the columnar body 81, beside the mounting groove 813. A first positioning slot 814 and a second positioning slot 816 are perpendicularly defined in the columnar body 81, extending through a circumferential surface of the columnar body 81. An access hole 818 along a center axis of the columnar body 81 is defined in a top of the columnar body 81 and communicates with the first positioning slot 814 and the second positioning slot 816. Each of the fixing members 83 includes two spaced through holes defined therein.

Referring to FIG. 1, the second friction block 90 is similar to the first friction block 80 and includes a first positioning slot 914, a second positioning slot 916, an access hole 918 is defined in a top of the second friction block 90 and communicates with the first positioning slot 914 and the second positioning slot 916.

Referring to also FIG. 4, to attach the friction bar 82 to the columnar body 81, the friction bar 82 engages in the mounting groove 812 of the columnar body 81. The fixing members 83 abut against the friction bar 82, and are fixed to the bottom of the columnar body 81 with a plurality of screws 801 extending the through holes of the fixing members 83 to engage in the fixing holes of the columnar body 81, therefore, the friction bar 82 is retained to the bottom of the columnar body 81 with a portion of the friction bar 82 protruding from the bottom of the columnar body 81.

Referring to FIGS. 1-5, in assembly, the supporting plate 40 is retained to the placing board 11 of the platform 10, and extends perpendicularly from the placing board 11 with the bottom edge 411 abutting against the placing board 11. The clamping members 22 are mounted to the positioning plate 21 of the first fixing assembly 20 along a side edge of the positioning plate 21 by screws. The clamping members 32 are mounted to the positioning plate 31 of the second fixing assembly 30 along the opposite lateral edges of the trapezoidal portion of the positioning plate 31 by screws. The positioning plate 21 of the first fixing assembly 20 and the positioning plate 31 of the second fixing assembly 30 are retained to the opposite lateral edges 413 of the supporting plate 40 by screws. The positioning plate 21 of the first fixing assembly 20 and the positioning plate 31 of the second fixing assembly 30 are perpendicular to the supporting plate 40, and respectively forms an angle of 45° relative to the placing board 11 of the platform 10. One pair of the reinforcing members 50 respectively abut opposite sidewalls of the supporting plate 40, and are sandwiched between the positioning plate 21 and the placing board 11, with the hypotenuse and one of the right-angle sides of each of the reinforcing members 50 respectively abutting against the placing board 11 and the positioning plate 21. The other one pair of the reinforcing members 50 respectively abut opposite sidewalls of the supporting plate 40, and sandwiched between the positioning plate 31 and the placing board 11 with the hypotenuse and one of the right-angle sides of each of the reinforcing members 50 respectively abutting against the placing board 11 and the positioning plate 31. The coupling member 64 extends into the pivoting hole 613 of the swing pole 61 until the flange 641 abuts against the top wall 602. A screw 605 extends through the through hole 642 of the coupling member 64 to engage in the screw hole of the top edge of the connecting portion 42 of the supporting plate 40. Therefore, the swing pole 61 is horizontally mounted to the supporting plate 40 and capable of pivoting about the coupling member 64. The first friction block 80 and the second friction block 90 are respectively suspended on two opposite ends of the swing pole 61. The opposite ends of the swing pole 61 are respectively passed through the first positioning slot 814 of the first friction block 80 and the first positioning slot 914 of the second friction block 90. The second positioning slot 816 of the first friction block 80 and the second positioning slot 916 of the second friction block 90 respectively align with the coupling holes 611. One of the locking bars 62 passes through the second positioning slot 816 of the first friction block 80 and one of the coupling holes 611 of the swing pole 61. The other one of the locking bars 62 passes through the second positioning slot 916 of the second friction block 90 and the other one of the coupling holes 611 of the swing pole 61. The locking grooves 621 of the locking bars 62 respectively align with the screw holes 612 of the swing pole 61, the access hole 818 of the first friction block 80 and the access hole 918 of the second friction block 90. Two screws 606 respectively extend through the access holes 818, 918 of the first friction block 80 and the second friction block 90 to engage in the screw holes 612 and further extend into the locking grooves 621 of the locking bars 62, for preventing the locking bars 62 from disengaging from the swing pole 61. Therefore, the first friction block 80 and the second friction block 90 are respectively mounted to the opposite ends of the swing pole 61. An angle of 45° is defined between the central axis of the columnar body 81 of the first friction block 80 and the positioning plate 21. An angle of 45° is defined between a central axis of the second friction block 90 and the positioning plate 31. Heights of the first positioning slots 814, 914 and the second positioning slots 816, 916 of the first friction block 80 and the second friction block 90 are configured to be greater than those of the swing pole 61 and the locking bars 62. Thus, the first friction block 80 and the second friction block 90 are capable of sliding vertically. The raising blocks 63 are retained to the swing pole 61, with two screws 607 correspondingly passing through the oblong holes 631 of the raising blocks 63 to engage in the fixing holes 614 of the swing pole 61 and the sliding flanges of the raising blocks 63 abutting against the opposite sidewalls 601 of the swing pole 61. Two screws 608 respectively extend through two nuts 609 and engage in the screw holes 616 of the swing pole 61. The nuts 609 are tightened to the swing pole 61 to retain the screws 608 to the opposite end walls 604 of the swing pole 61. The positioning block 71 of the travelling limiting member 70 is attached to the rectangular connecting portion 42 of the supporting plate 40, with one of the lateral edges of the connecting portion 42 engaging in the engaging groove 7121 of the positioning block 71. A screw (not shown) is passed through the securing hole 7122 of the positioning block 71 to engage in the corresponding screw hole defined in the lateral edges of the connecting portion 42 to retain the positioning block 71 to the supporting plate 40. The travelling limiting member 70 bestrides a lower portion of the swing pole 61. Two screws 73 respectively extend through two nuts 75 and the screw holes 7141 of the blocking portions 714, with distal ends of the screws 73 respectively extending toward opposite sidewalls 601 of the swing pole 61.

Referring to FIG. 6, to measure the coating adhesive strengths of the edge 101 of the first object 100 and the corner 201 of the second object 200, the first object 100 and the second object 200 are respectively fixed by the first fixing assembly 20 and the second fixing assembly 30. The first object 100 is retained to the positioning plate 21 by the clamping members 22. The friction bar 82 of the first friction block 80 abuts against the edge 101 of the first object 100 by an action of gravity of the first friction block 80. The second object 200 is retained to the positioning plate 31 by the clamping members 32. The corner 201 of the second object 200 is aligned with a top edge of the trapezoidal portion of the positioning plate 31. A bottom of the second friction block 90 abuts against the corner 201 of the second object 200 by an action of gravity of the second friction block 90. Each of the screws 73 is operated to adjust a distance between the distal end thereof and the swing pole 61. Accordingly, the pivoting scope of the swing pole 61 and the traveling distance of the first friction block 80 and the second friction block 90 are determined.

At least one screw 608 is manipulated to rotate the swing pole 61 clockwise and anticlockwise about the coupling member 64. In this process, rotating directions of the swing pole 61 shift when the opposite sidewalls 601 of the swing pole 61 contact the distal ends of the screws 73 of the travelling limiting member 70. Thus, the first friction block 80 and the second friction block 90 respectively scratch the edge 101 of the first object 100 and the corner 201 of the second object 200 back and forth over a predetermined count. The coating adhesive strengths of the edge 101 of the first object 100 and the corner 201 of the second object 200 are evaluated according to the surface status of the edge 101 of the first object 100 and the corner 201 of the second object 200.

When only the first object 100 is to be tested, the right raising block 63 is used to raise the second friction block 90 for avoiding interference with the second fixing assembly 30. The narrow portion of the right raising block 63 is slid into the first positioning slot 914 of the second friction block 90, with the corresponding screw 607 located in the left of the corresponding oblong hole 631. Similarly, when only the second object 200 is to be tested, the left raising block 63 is used to raise the first friction block 80 for avoiding interference with the first fixing assembly 20. The narrow portion of the left raising block 63 is slid into the first positioning slot 814 of the first friction block 80, with the corresponding screw 607 located in the right of the corresponding oblong hole 631.

It is believed that the present embodiment and its advantages will be understood from the foregoing description, and it will be apparent that various changes may be made thereto without departing from the spirit and scope of the description or sacrificing all of its material advantages, the example hereinbefore described merely being exemplary embodiments.

What is claimed is:

1. An adhesion measuring apparatus to measure a coating adhesive strength of an edge or a corner of at least one object, the measuring apparatus comprising:
   a platform;
   a supporting plate mounted to the platform;
   a loading mechanism pivotably mounted to the supporting plate;
   a friction block attached to the loading mechanism;
   a fixing assembly configured for positioning the object such that the friction block slidably abuts against and reciprocatingly rubs the edge or corner of the object within a predetermined traveling distance; and
   a travelling limiting member connected to the supporting plate to limit a pivoting angle of the loading mechanism to limit the predetermined traveling distance.

2. The measuring apparatus of claim 1, wherein the fixing assembly comprises a positioning plate supporting the object, and at least one clamping member securing the object to the positioning plate.

3. The measuring apparatus of claim 2, wherein the supporting plate comprises a lateral edge slanting to the platform, the positioning plate of the fixing assembly abuts against and is fixed to the supporting plate.

4. The measuring apparatus of claim 3, wherein the platform comprises a horizontal placing board, the supporting plate vertically extends from the placing board with an angle of about 45° defined between the lateral edge of the supporting plate and the placing board.

5. The measuring apparatus of claim 1, wherein the friction block defines a first positioning slot, the loading mechanism comprises a swing pole pivotably connected to the supporting plate and passing through the positioning slot of the friction block.

6. The measuring apparatus of claim 5, wherein the friction block defines a second positioning slot intersecting with the first positioning slot, the swing pole defines a coupling hole, the loading mechanism comprises a locking bar passing through the second positioning slot of the friction block and the coupling hole of the swing pole.

7. The measuring apparatus of claim 1, wherein the travelling limiting member comprises a substantially U-shaped positioning block comprising a mounting portion engaging with the supporting plate and a pair of blocking portions perpendicularly extending from opposite ends of the mounting portion, the travelling limiting member bestrides across the loading mechanism with the blocking portions spacedly located at opposite sides of the loading mechanism.

8. The measuring apparatus of claim 7, wherein two screw holes are respectively defined in the blocking portions of the positioning block of the travelling limiting member, the travelling limiting member further comprises a pair of screws engaging in the screw holes of the blocking portions of the positioning block.

9. A measuring apparatus to measure the adhesion strength of an edge of a first object and a corner of a second object, the measuring apparatus comprising:
   a platform;
   a supporting plate mounted to the platform;
   a loading mechanism pivotably mounted to the supporting plate;
   a first friction block and a second friction block mounted to opposite ends of the loading mechanism;
   a first fixing assembly configured for positioning the first object such that the first friction block slidably abuts against and reciprocatingly rubs the edge of the first object within a predetermined traveling distance;
   a second fixing assembly for positioning the second object such that the second friction block slidably abuts against and rubs the corner of the second object within the predetermined traveling distance; and
   a travelling limiting member connected to the supporting plate to limit a pivoting angle of the loading mechanism to limit the predetermined traveling distance.

10. The measuring apparatus of claim 9, wherein loading mechanism comprises a swing pole pivotably connected to the supporting plate and two raising blocks slidably engaging with the swing pole, one of the raising blocks is retractably sliding into the first friction block to keep the first friction disengaging with the first fixing assembly, the other raising block is retractably sliding into the second friction block to keep the second friction disengaging with the second fixing assembly.

11. The measuring apparatus of claim 9, wherein each of the first fixing assembly and the second fixing assembly comprises a positioning plate, the positioning plate of the first fixing assembly is rectangular with an side edge aligning with the edge of the first object, the positioning plate of the second fixing assembly comprises a trapezoidal portion with a top edge aligning with the corner of the second object.

12. The measuring apparatus of claim 9, wherein the first friction block comprises a columnar body engaging with loading mechanism and a friction bar attached to a bottom of the columnar body to abut against the edge of the first object.

* * * * *